(12) United States Patent
Porter et al.

(10) Patent No.: US 8,114,807 B2
(45) Date of Patent: Feb. 14, 2012

(54) SYNTHESIS AND USE OF INTERMETALLIC IRON PALLADIUM NANOPARTICLE COMPOSITIONS

(75) Inventors: Keith A. Porter, Monroe, NC (US); E. Keller Barnhardt, Charlotte, NC (US)

(73) Assignee: CEM Corporation, Matthews, NC (US)

(*) Notice: Subject to any disclaimer, the term of this patent is extended or adjusted under 35 U.S.C. 154(b) by 0 days.

(21) Appl. No.: 12/718,319

(22) Filed: Mar. 5, 2010

(65) Prior Publication Data

US 2011/0218364 A1 Sep. 8, 2011

(51) Int. Cl.
*B01J 23/00* (2006.01)
*B01J 21/00* (2006.01)

(52) U.S. Cl. ........ 502/338; 502/326; 502/333; 502/336; 502/339

(58) Field of Classification Search ............ 502/327, 502/333, 336, 338, 339, 326; 977/773
See application file for complete search history.

(56) References Cited

U.S. PATENT DOCUMENTS

| | | | |
|---|---|---|---|
| 4,904,700 A * | 2/1990 | Sapienza et al. ............ 518/700 |
| 7,022,256 B2 * | 4/2006 | Uegami et al. ............ 252/181 |
| 7,208,134 B2 * | 4/2007 | Bromberg et al. ......... 423/592.1 |
| 7,247,598 B2 | 7/2007 | Duan et al. |
| 7,410,625 B2 * | 8/2008 | Sun ............................ 423/138 |
| 7,510,993 B2 * | 3/2009 | Levey et al. ............... 502/150 |
| 7,803,734 B2 * | 9/2010 | Majima et al. ............. 502/185 |
| 7,947,191 B2 * | 5/2011 | Wang et al. .............. 252/62.55 |
| 7,960,025 B2 * | 6/2011 | Fernandez Camacho et al. .......................... 428/403 |
| 2002/0160190 A1 | 10/2002 | Yadav et al. |
| 2005/0130838 A1 | 6/2005 | Duan et al. |
| 2006/0182997 A1 * | 8/2006 | Yamamoto et al. ........ 428/692.1 |
| 2008/0181843 A1 | 7/2008 | Lu et al. |
| 2008/0245186 A1 * | 10/2008 | Yang et al. ..................... 75/362 |
| 2009/0124834 A1 * | 5/2009 | Wang et al. .................. 564/422 |
| 2010/0056363 A1 * | 3/2010 | Lee .............................. 502/167 |
| 2011/0036705 A1 | 2/2011 | Barclay et al. |

FOREIGN PATENT DOCUMENTS

| | | |
|---|---|---|
| CN | 101011669 A | 8/2007 |
| WO | 2004009233 A1 | 1/2004 |
| WO | 2008156320 A1 | 12/2008 |
| WO | 2009015890 A2 | 2/2009 |

OTHER PUBLICATIONS

Nguyen et al., "Synthesis of monodispersed fcc and fct FePt/FePd nanoparticles by microwave irradiation," Journal of Materials Chemistry, 2005, vol. 15, pp. 5136-5143.

Petkov et al., "Atomic-Scale Structure of Nanocrystals by High-Energy X-ray Diffraction and Atomic Pair Distribution Function Analysis: Study of FexPd100-x (x= 0, 26, 28, 48) Nanoparticles," J. Phys. Chem. C, 2007, vol. 111, No. 2, pp. 714-720.

(Continued)

*Primary Examiner* — Cam N. Nguyen
(74) *Attorney, Agent, or Firm* — Summa, Additon & Ashe, P.A.

(57) ABSTRACT

An intermetallic magnetic compound of iron oxide and palladium with a nanometer particle size is disclosed, together with a method of making magnetic nanoparticles that include an intermetallic bond between palladium and iron-oxide. Additionally, a method is disclosed of catalyzing an organic reaction by contacting the organic reagents with an intermetallic magnetic compound of iron oxide and palladium that has nanometer particle size in an amount sufficient to catalyze the organic reaction.

11 Claims, 6 Drawing Sheets

OTHER PUBLICATIONS

Teranishi et al., "Conversion of Anisotropically Phase-Segregated Pd/y-Fe2O3 Nanoparticles into Exchange-Coupled fct-FePd/a-Fe Nanocomposite Magnets," JAMS, 2008, vol. 130, pp. 4210-4211.

Shao et al., "Pd—Fe Nanoparticles as Electrocatalysts for Oxygen Reduction," JAMS, 2006, vol. 128, pp. 3526-3527.

Hou et al., "Preparation and Characterization of Monodisperse FePd Nanoparticles," Chem. Mater., 2004, vol. 16, No. 24, pp. 5149-5152.

Qadri et al., "Structural and magnetic properties of nano-crystalline FePd alloys prepared by organo-metallic synthesis," Applied Physics A, 2005, vol. 81, pp. 587-590.

Nazir et al., "Superparamagnetic bimetallic iron-palladium nanoalloy: synthesis and characterization," Nanotechnology 19, 2008, pp. 1-6.

U.S. Appl. No. 12/541,262, filed Aug. 14, 2009 for Pressure-Stepped Microwave-Assisted Digestion—Application Publication No. 2011-0036705.

Kalinkin et al., Mechanism of low-temperature CO oxidation on a model Pd/Fe2O3 catalyst; Catalysis Letters 59, 1999, pp. 115-119.

Zhao et al., "The leaching and re-deposition of metal species from and onto conventional support palladium catalysts in the Heck reaction of iodobenzene and methyl acrylate in N-methylpyrrolidone," Journla of Molecular Catalysis A: Chemical 180, 2002, pp. 211-219.

Schalow et al., "Oxygen Storage at the Metal/Oxide Interface of Catalysit Nanoparticles," Angewandte Chemie Int. Ed., 2005, 44, pp. 7601-7605.

Edwards et al., "Direct synthesis of hydrogen peroxide from H2 and O2 using Au—Pd/Fe2O3 catalysts," Journal of Materials Chemistry, 2005, 15, pp. 4595-4600.

Stevens et al., "Recycling of homogeneous Pd catalysts using superparamagnetic nanoparticles as novel soluble supports for Suzuki, Heck, and Sonogashira cross-coupling reactions," Chem. Comm., 2005, pp. 4435-4437.

Wang et al., "Synthesis of palladium-coated magnetic nanoparticle and its application in Heck reaction," Colloids and Surfaces A: Physicochem. Eng. Aspects 276, 2006, pp. 116-121.

Hara et al., "Magnetically recoverable heterogeneous catalyst: Palladium nanocluster supported on hydroxyapatite-encapsulated y -Fe2O3 nanocrystallites for highly efficient dehalogenation with molecular hydrogen," Green Chem, 2007, 9, pp. 1246-1251.

Jiang et al., "A novel nanoscale catalyst system composed of nanosized Pd catalysts immobilized on Fe3O4@SiO2-PAMAM," Nanotechnology 19, 2008, pp. 1-6.

Jiang, et al, "Synthesis of Pd/a-Fe2O3 nanocomposites for catalytic CO oxidation," Journal of Materials Processing Technology 209, 2009, pp. 4558-4562.

Giordano et al., "Charging of Metal Adatoms on Ultrathin Oxide Films: Au and Pd on FeO/Pt(111)," The American Physical Society, Physical Review Letters, 101, 2008, pp. 026102-1-026102-4.

MacDonald et al., "Removal of Residual Metal Catalysts with Iron/Iron Oxide Nanoparticles from Coordinating Environments," American Chemical Society, 2008, 24, pp. 7169-7177.

Liu et al, "Magnetically Separable Pd Catalyst for Carbonylative Sonogashira Coupling Reactions for the Synthesis of a,B-Alkynyl Ketones," American Chemical Society, Organic Letters, 2008, vol. 10, No. 18, pp. 3933-3936.

Krehula et al., "Formation of iron oxides in a highly alkaline medium in the presence of palladium ions," Journal of Molecular Structure 924-926, 2009, pp. 201-207.

Polshettiwar et al., "Nanoparticle-supported and magnetically recoverable palladium (Pd) catalyst: a selective and sustainable oxidation protocol with high turnover number," Organic and Biomolecular Chemistry, 2009, 7, pp. 37-40.

Polshettiwar et al., "Self-Assembly of Metal Oxides into Three-Dimensional Nanostructures: Synthesis and Application in Catalysis," ACS Nano, Feb. 11, 2009.

* cited by examiner

Controlled temperature and pressure for Pd-Fe2O3 intermetallic compound

Fig. 4 XPS

SYNTHESIS AND USE OF INTERMETALLIC IRON PALLADIUM NANOPARTICLE COMPOSITIONS

BACKGROUND

The present invention relates to the synthesis, characterization, and use of intermetallic magnetic iron-palladium nanoparticles, particularly as magnetically recoverable catalysts.

In its classical definition, a catalyst is a composition (typically an element or compound) that increases the rate of an underlying chemical reaction without participating as a reactant or a product in the reaction and thus without being used up as the reaction proceeds.

Although this definition is accurate and appropriate on a theoretical and molecular level, when used in larger (e.g., "commercial" or "scale up") amounts, catalysts can present practical difficulties along with their rate-enhancing advantages.

Many catalysts are described as being either homogeneous or heterogeneous. A homogeneous catalyst operates in the same phase as the reaction that it catalyzes. For example, in a reaction that takes place in solution, a homogeneous catalyst is also soluble in that solution. Homogeneous catalysts have advantages, particularly in terms of selectivity, but because they operate in the same phase as the reaction, they are more prone to degradation and they are almost impossible to recover and reuse.

In this regard, a catalyst is considered advantageous if it can be recovered and reused multiple times without significant difficulty and while maintaining a high degree of catalytic performance. Such characteristics are sometimes quantified using the "turnover number" which represents the number of times a catalyst can be used while maintaining a specified level of catalytic activity, often measured by product yield.

Heterogeneous catalysts are present in a different phase from the reactions that they catalyze. As a result, they can be somewhat easier to recover, but because of the phase difference, they can be somewhat less selective than similar homogeneous catalysts and can be sterically hindered in some circumstances. Additionally, even though heterogeneous catalysts can be somewhat easier to recover than homogeneous catalysts, they still require physical recovery steps such as filtration or centrifuging. Furthermore, because a heterogeneous catalyst typically includes the catalyzing element (often a metal) on a physical support (carbon being exemplary), the catalyst can become dissociated from the support during the reaction and thus can be difficult to remove from the final product. This is sometimes referred to as the catalyst leaching.

As one example, when palladium catalysts (e.g., palladium catalysts on carbon supports) are used in the synthesis of pharmaceutical products in scale up (i.e., commercially viable) amounts, palladium metal has a tendency to leach from the support. When separated from the support, the palladium can remain behind as an undesired contaminant in the final product when the support is removed. The presence of biologically-active amounts of heavy metals such as palladium is, of course, usually unacceptable in a pharmaceutical product.

Thus, when the final product of the catalyzed reaction is, for example, a pharmaceutical composition and the catalyst is a heavy metal, the presence of the leftover heavy metal catalyst must be either eliminated or reduced to acceptable amounts, which typically are in the parts per million (ppm) range or less.

As an additional problem, the carbon used to support the palladium catalyst also has a tendency to absorb undesired compositions as the underlying reaction proceeds. This in turn can make the catalyst support unacceptable for future use and can create another disposal problem.

Palladium is nevertheless a preferred catalyst for a number of organic reactions including reactions that are important in the synthesis of higher complexity organic molecules. Examples include (but are not limited to) the Suzuki, Heck, and Sonogashira reactions.

The Suzuki reaction is a coupling reaction between an aryl halide and an aryl boronic acid catalyzed by palladium metal. The Heck reaction is the chemical reaction of an unsaturated halide with an alkene and a strong base using a palladium catalyst to form a substituted alkene. The Sonogashira reaction is a coupling of terminal alkynes with aryl or vinyl halides for which palladium and copper are the catalysts.

Accordingly, a need exists for heterogeneous catalysts that are recoverable, reusable (the terms have slightly different meanings in this art), active, can be readily synthesized, and that are appropriate for scale-up synthesis.

In many cases, magnetic particles offer advantages for heterogeneous catalyst support (among other uses) because they can be easily separated using an external magnetic field. This provides an easier work up procedure that tends to recover all of the solid catalyst in the separation procedure.

Such particles, including nanometer-scale magnetic, solid supported palladium catalysts, are typically formed by one of three different methods and form three somewhat different types of compositions. In a number of cases, an iron composition—often an iron oxide—provides the desired magnetic characteristics.

In the first method, referred to as "deposition/impregnation", the catalyst (e.g., palladium) is produced by a technique that places the palladium compound on the desired support. In such compositions the palladium is physically attached to the carrier (e.g., iron oxide) rather than chemically bonded to it. As a result, when impregnated catalysts are in use, palladium tends to constantly dissociate from the support and leach into the products, leading in turn to the need to remove the palladium from the desired product.

In the second method, the palladium is covalently bonded, often through organic ligands to an iron oxide support. Although the covalent bond is typically stronger than the physical attraction in the impregnated catalysts, the covalent bond will tend to dissociate under reaction conditions and produce undesired palladium in the reaction product.

Impregnated or covalently bonded magnetic solid supported palladium catalysts are relatively easy to prepare, recover and reuse. As disadvantages, however, the preparation steps usually involve coating or functionalizing steps and are often time-consuming.

In the third method an intermetallic compound is formed that includes the desired catalyst metal. Because of the metal-metal bond, such intermetallic compounds minimize or eliminate leaching. This also makes such catalysts more readily reusable.

As potential disadvantages, however, typical routes for producing intermetallic iron palladium nanoparticles require the use of iron carbonyl ($Fe(CO)_5$) which is extremely toxic and sensitive to exposure to air, characteristics that make iron carbonyl dangerous and inconvenient to work with. Many intermetallic iron-palladium synthesis routes also require higher temperatures in a toxic high boiling point solvent, or annealing at high temperatures (above 500° C.) for up to 15 hours in a mixture of argon and hydrogen gases, or both.

Accordingly, a less toxic ("greener") approach to obtaining magnetic palladium-iron nanoparticles would provide advantages during synthesis of the nanoparticles as well as during their use in catalyzing reactions and in recovering the catalyst from the reaction products easily and while minimizing or eliminating the problems caused by palladium bleaching or carbon absorption.

SUMMARY

In one aspect, the invention is an intermetallic magnetic compound of iron oxide and palladium with a nanometer particle size.

In another aspect, the invention is a method of making magnetic nanoparticles that include an intermetallic bond between palladium and iron-oxide In yet another aspect, the invention is a method of catalyzing an organic reaction by contacting the organic reagents with an intermetallic magnetic compound of iron oxide and palladium that has nanometer particle size in an amount sufficient to catalyze the organic reaction.

The foregoing and other objects and advantages of the invention and the manner in which the same are accomplished will become clearer based on the followed detailed description taken in conjunction with the accompanying drawings.

DETAILED DESCRIPTION

Figure 1:
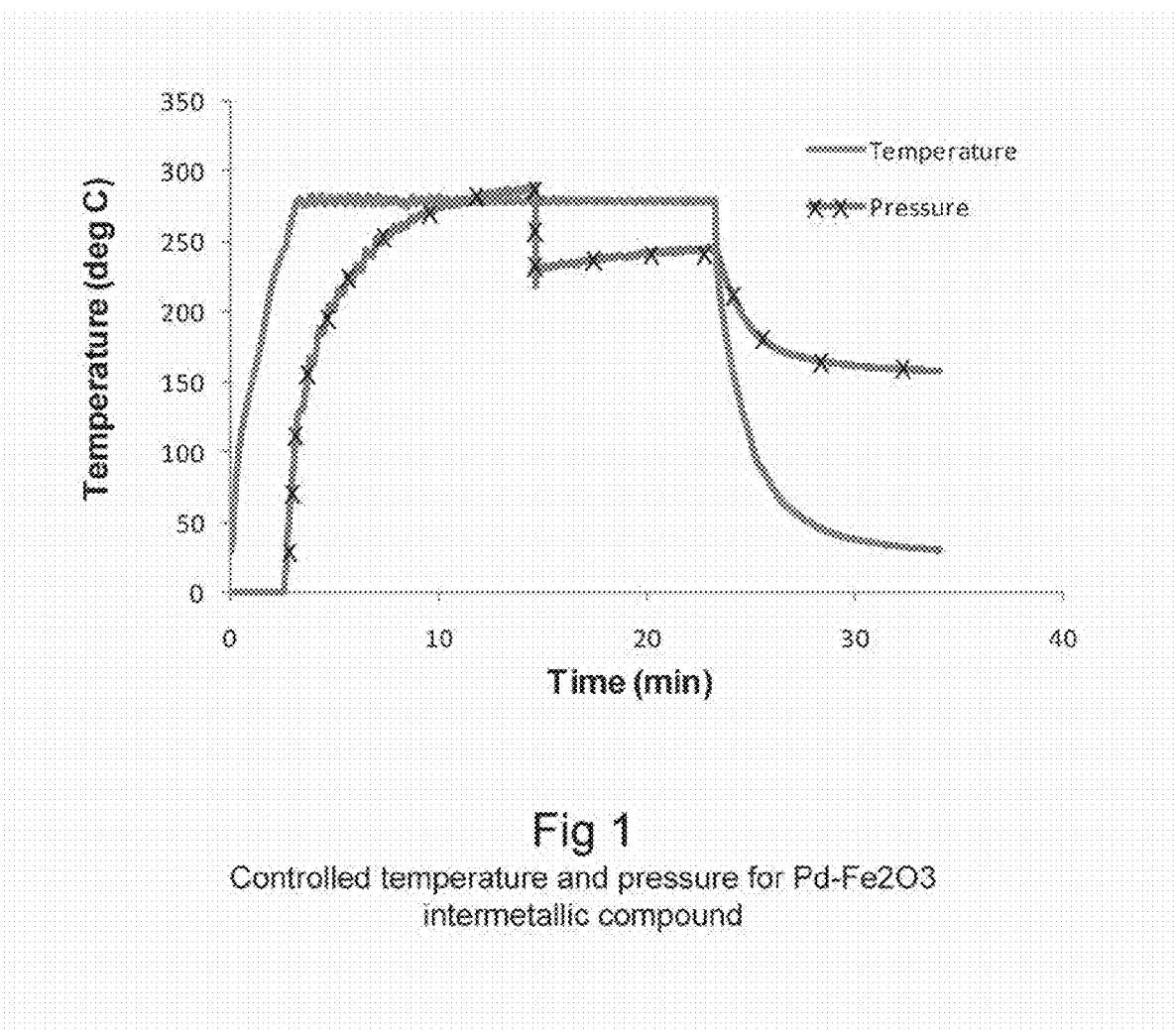
FIG. 1 is a plot of the controlled temperature and pressure for the synthesis of a palladium-iron oxide intermetallic compound according to the present invention.

The present invention encompasses a nanometer scale particulate composition of iron and palladium that demonstrates magnetic properties. The invention also encompasses a synthesis route for obtaining a composition as well as the use of the composition as a solid support catalyst.

The catalytic use of the composition is exemplary rather than limiting. Magnetic nanoparticles are of interest in a number of additional applications such as data storage, medicine, imaging and environmental remediation. Thus, although much of the description herein deals with catalysts, in its synthesis and composition aspects, the invention also includes these other potential applications.

In one embodiment, the invention is a composition comprising an intermetallic magnetic compound of iron oxide and palladium with a nanometer particle size. As used herein, the term intermetallic means that a chemical bond exists between iron and palladium in this composition; i.e., in contrast to other compositions in which iron and palladium are present, but not bonded to one another.

The magnetic characteristics are consistent with well-recognized definitions and can be measured and confirmed using (for example) a vibrating sample magnetometer (VSM).

As is further conventional, the term "nanometer particle size" refers to particles that are less than 200 nanometers (nm) in their largest dimension. In the described embodiments, the particle size was determined photographically. On that basis about 90% of the particles were about 6 nm.

In exemplary embodiments the iron oxide is predominately $Fe_2O_3$, but the composition is not limited to this particular stoichiometry.

In exemplary embodiments the composition also can be expressed in terms of the following formula:

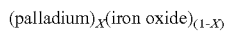

$$(\text{palladium})_X(\text{iron oxide})_{(1-X)}$$

and in which X is at least 0.7. In some embodiments X is at least about 0.9. This can also be expressed as composition in which the mole fraction of palladium is at least about 0.7 or at least about 0.9.

As a further advantage, particularly in the catalyst context, at least about 70% by weight—and in exemplary embodiments at least about 90% by weight—of the palladium present is present on the surface of the nanometer size particles.

In exemplary embodiments, the particle size is below 50 nm, in other embodiments below 20 nm, and in particular embodiments, between about 5 and 10 nm.

Because the composition according to the invention is useful as a catalyst, in another aspect, the invention is a method of catalyzing organic reactions. In this aspect, the invention includes adding the composition as a catalyst to an organic reaction in an amount sufficient to catalyze the reaction. As set forth in the examples herein, the composition is particularly effective as a catalyst for organic coupling and hydrogenation reactions, and it is expected that the composition will likewise have a successful application for other organic reactions for which palladium is a useful or preferred catalyst.

In another aspect, the invention includes a method of making magnetic nanoparticles that include an intermetallic bond between palladium and iron oxide. In this aspect, the method comprises combining an iron coordination compound in which the ligand includes oxygen with a palladium coordination compound in which the ligand includes oxygen with the proviso that the iron coordination compound is other than iron carbonyl.

The coordination compounds are combined in the presence of at least one surfactant in an organic solvent. In exemplary embodiments, the surfactant is nonionic; i.e., the surfactant does not dissociate into ions in aqueous solutions.

The reactants are irradiated with microwave energy sufficient for the iron and palladium coordination compounds to react, with controlled application of a single mode of microwave radiation being a useful embodiment. During the reaction, the temperature and pressure are moderated to produce a magnetic intermetallic compound of palladium and iron oxide without degrading the surfactant or the solvent.

The iron and palladium coordination compounds can include any ligand that produces the magnetic nanoparticles without adversely affecting the reaction or the desired product. In some embodiments, the coordination compound is selected from the group consisting of $FeCl_3$, Ferrocene (Fe$(C_5H_5)_2$), $Fe(NO_3)_3$, $PdCl_2$, $Na_2PdCl_4$, $Pd(OAc)_2$, and $PdCl_2(PPh_3)_2$. In particular, $FeCl_3$:$Pd(OAc)_2$, $Fe(acac)_2$:$Pd(OAc)_2$, and Fe(NO$_3$)$_3$ with Pd(OAc)$_2$ or Pd(acac)$_2$ gave magnetic particles. Upon prolonged heating, the Fe(NO$_3$)$_3$ gave the resulting nanoparticles.

In exemplary embodiments, the iron coordination compound is iron 2,4-pentanedione (acetylacetone, "acac") and the palladium coordination compound is palladium 2, 4-pentanedione. These are typically abbreviated as Fe(acac)$_2$ and Pd(acac)$_2$. Among the tested ligands, Pd(acac)$_2$ with Fe(acac)$_2$ had the highest yield with the shortest reaction time. The ratio of Pd(acac)$_2$ to Fe(acac)$_2$ appears to be important. A Fe:Pd ratio of 1:4 appears to be ideal, while ratios of 1:1 and 2:1 failed to produce magnetic particles.

Persons of skill in this art may be able to incorporate other ligands not yet specifically tested or listed herein that are also entirely appropriate in synthesizing the particles according to the present invention.

The non-ionic surfactant is typically selected from the group consisting of alcohol ethoxylates, alkylphenol ethoxylates, phenol ethoxylates, amide ethoxylates, glyceride ethoxylates, soya bean oil and caster oil ethoxylates, fatty acid ethoxylates, fatty amine ethoxylates, and alkyl glycosides in which the hydrophilic groups are sugars (polysaccharides).

In exemplary embodiments, the non-ionic surfactant is selected from the group consisting of oleic acid, oleyl amine and combinations thereof. In the embodiments and examples described herein, the surfactant includes both oleic acid and oleyl amine.

As understood by persons of skill in this art, the characteristics and amount of the surfactant—potentially including the presence and ratio of two or more surfactant—can affect the growth of the nanocrystals including the particle shape.

In exemplary embodiments the organic solvent is a glycol, with polyethylene glycol being used successfully in the examples described herein.

During synthesis of the magnetic nanoparticles, the pressure generated by the reaction is periodically reduced in order to maintain the temperature of the reaction below about 300° C. Using the relationship between pressure and temperature established by the well-understood gas laws (the ideal gas law is exemplary), the pressure is released in defined intervals in order to keep the temperature—which is, of course, directly proportional to the pressure—within a desired range. A method of carrying this out and an associated instrument are described for example in commonly assigned and co-pending U.S. application Ser. No. 12/541,262 filed Aug. 14, 2009 for "Pressure-Stepped Microwave-Assisted Digestion" and now Publication No. 20110036705. The contents of Ser. No. 12/541,262 are incorporated entirely herein by reference.

The temperature is, however, generally maintained above 200° C. in order to encourage the reaction to proceed.

Stated functionally, as an upper limit, the temperature is maintained as high as possible without degrading the solvent or the surfactants, which are typically the first constituents to be adversely affected at temperatures above 300° C. The lowest temperature would, of course, be defined by the temperature required to overcome the energy of activation to thereby initiate and carry out the reaction.

Based upon the method, in another aspect, the invention includes the magnetic nanoparticles that have an intermetallic bond between palladium and iron oxide formed according to the precedingly described method.

In yet another aspect, the invention includes a method of catalyzing an organic reaction. In this aspect, the invention comprises contacting selected organic reagents with an intermetallic magnetic compound of iron oxide and palladium that has nanometer particle size and in an amount sufficient to catalyze the organic reaction.

In exemplary embodiments the method comprises catalyzing organic coupling and hydrogenation reactions. It is expected, however, that the catalyzing method according to the invention can be successfully used to catalyze many, and potentially a majority, of reactions that are successfully catalyzed with palladium.

In exemplary embodiments, the method comprises contacting the organic reagents with a compound in which the iron oxide is predominately Fe$_2$O$_3$, the mole fraction of palladium in the catalyst is at least about 0.70, at least about 70% by weight of the palladium is present on the surface of the nanometer size particles, and the particle size is below 20 nm.

As set forth in the experimental section, in additional embodiments, the mole fraction of palladium in the catalyst is at least about 0.9, at least about 90% by weight of the palladium is present on the surface of the nanometer size particles, and the particle size is between about 8 and 11 nm.

EXPERIMENTAL

Example 1

In an exemplary reaction, 0.20 millimoles of iron 2,4-pentanedione (e.g., "acetylacetone" or "acac"; Fe(acac)$_2$) were combined with 0.80 millimoles of palladium 2,4-pentanedione (Pd(acac)$_2$). The reagents were placed in a microwave transparent vessel in a CEM DISCOVER® instrument (CEM Corporation, Matthews, N.C., USA) and were irradiated using 300 watts of power at (frequency 2.45 GHz; wavelength 12.2 cm) for 20 minutes with intermediate pressure release to maintain a maximum temperature of about 280° C. The reaction was carried out in polyethylene glycol (PEG) as the solvent and in the presence of 1.6 millimoles of oleic acid and 0.80 millimoles of oleyl amine (9-octadecenylamine). Under these conditions, the reaction produced between about 120 and 150 milligrams of palladium-iron oxide nanoparticles which represented a yield of approximately 50% based on weight.

FIG. 1 is a plot of the temperature and pressure protocol for this example. As indicated by the two lines, the pressure was partially released after approximately 15 minutes of reaction time in order to help maintain the desired temperature.

Figure 2:
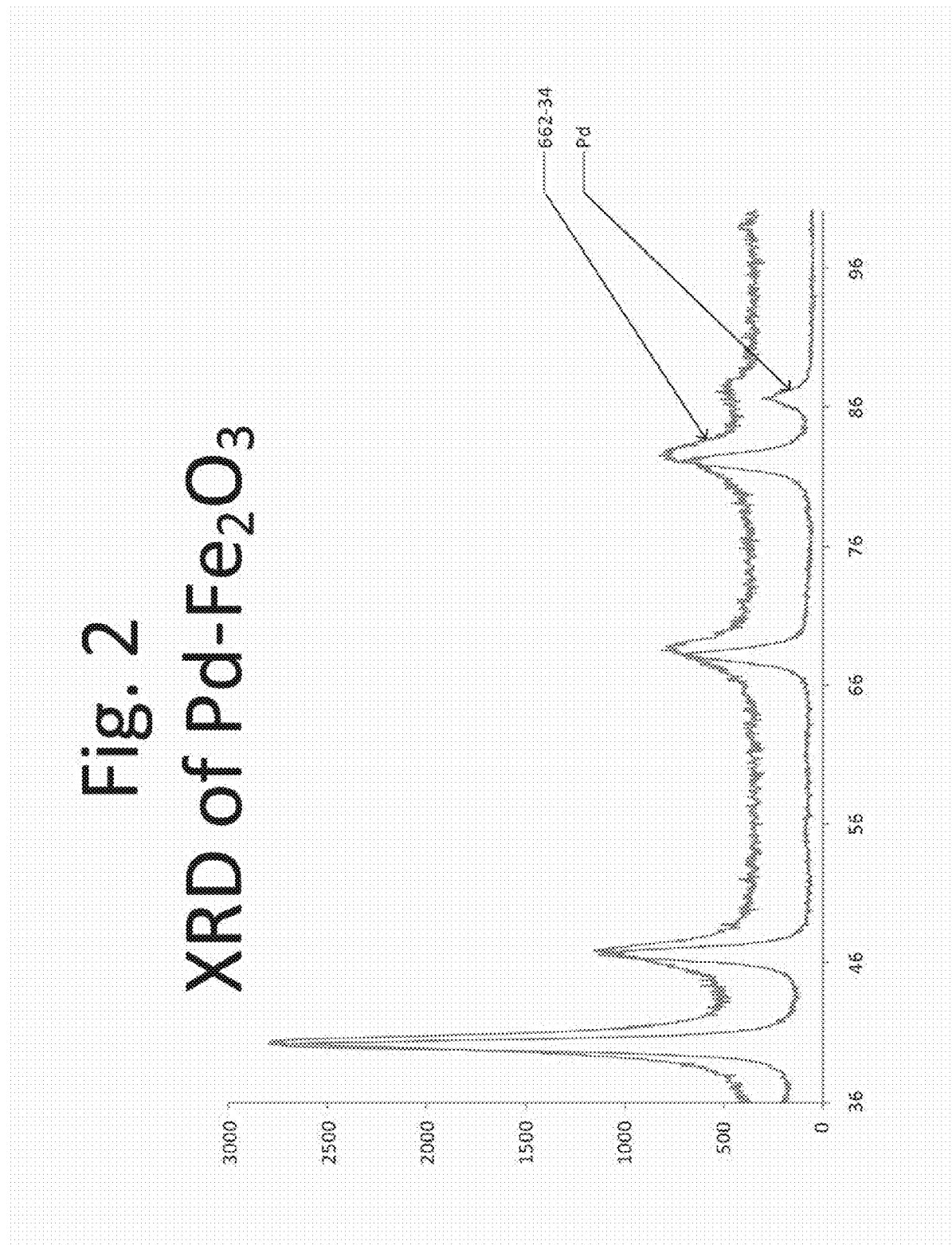
FIG. 2 is the x-ray diffraction spectra of palladium and of a palladium iron oxide intermetallic compound according to the invention.

The resulting particles were characterized by several physical tests. FIG. 2 is the x-ray diffraction spectrum of the resulting palladium-iron oxide compound in which the upper portion of the spectrum represents the palladium-iron oxide composition and the lower portion represents metallic palladium. As indicated by the peaks near 40, 67 and 82, and 86, the diffraction of the palladium is shifted to a higher angle in a manner consistent with the presence of an intermetallic bond between the palladium and the iron oxide.

Figure 3:
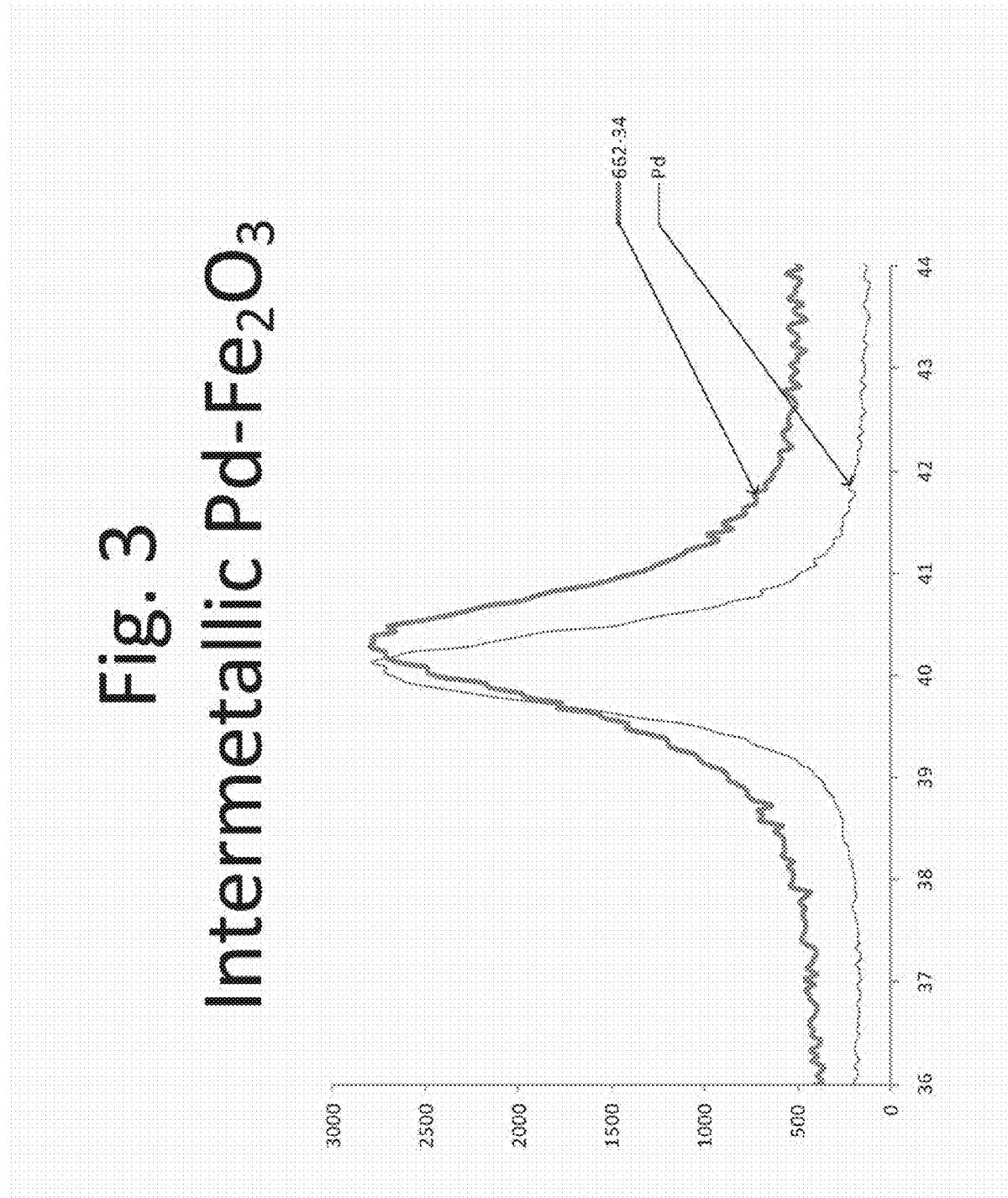
FIG. 3 is an enlarged portion of the x-ray diffraction spectra of FIG. 2.

FIG. 3 is an enlarged portion of the respective x-ray diffraction spectra of FIG. 2 showing both metallic palladium and the palladium-iron oxide composition formed by the precedingly-described reaction. The palladium peak in the composition is again shifted to a higher angle illustrating the presence of an intermetallic bond between the palladium and the iron oxide.

Figure 4:
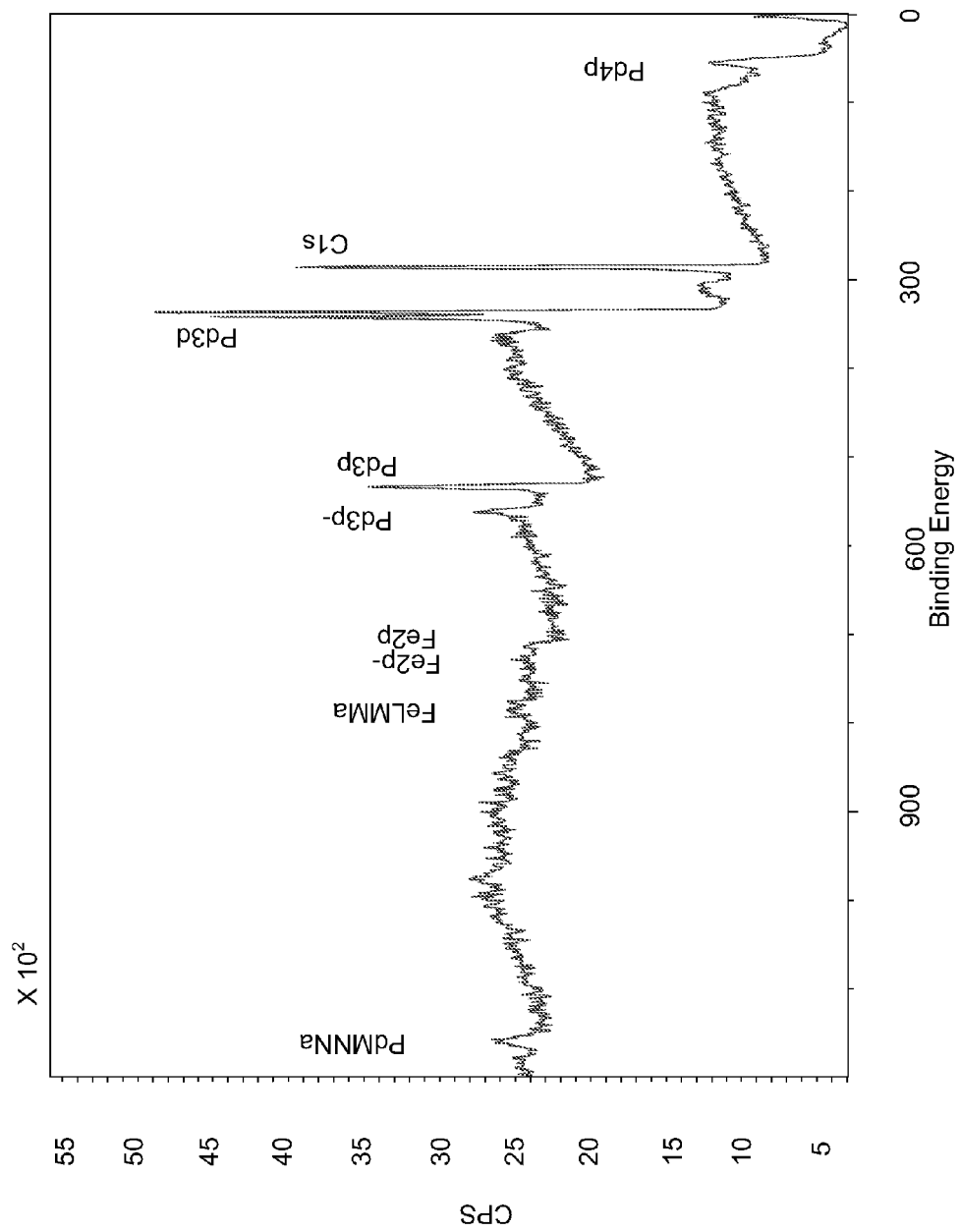
FIG. 4 is an x-ray photoelectron spectrum of the palladium-iron oxide compound according to the present invention.
Figure 5:
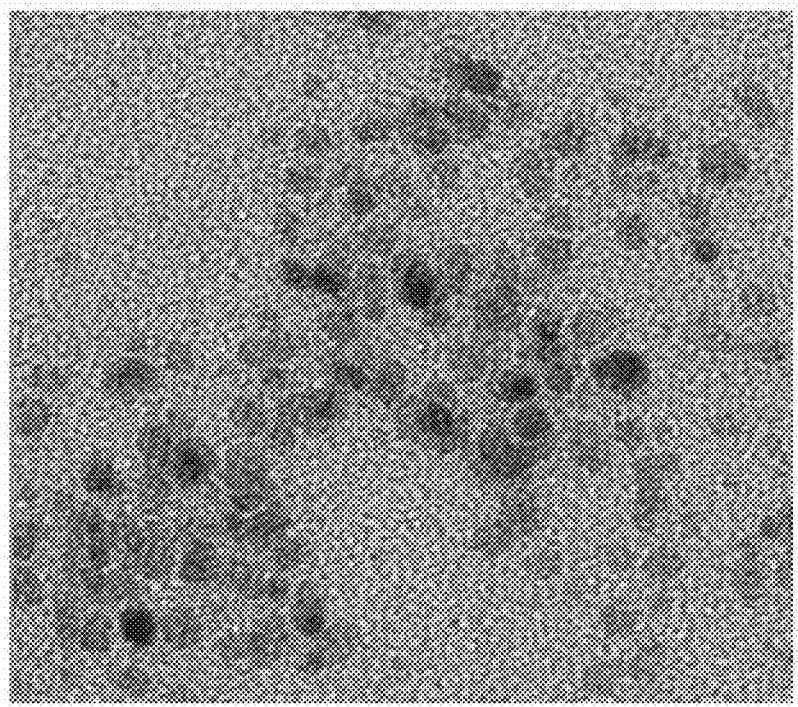
FIG. 5 is a photograph of particles according to the present invention synthesized using microwave irradiation.
Figure 6:
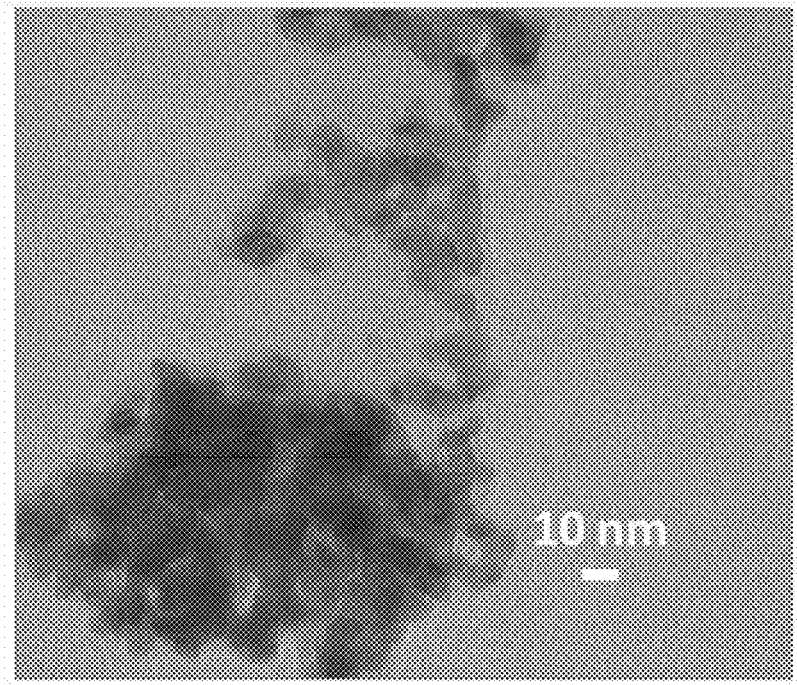
FIG. 6 is a photograph of particles according to the present invention synthesized using conventional heating.

FIG. 4 is the x-ray photoelectron spectroscopy (xps) spectrum of the palladium-iron oxide composition formed in Example 1. As recognized by persons of skill in this art, x-ray photoelectron spectroscopy is carried out by irradiating a sample with x-rays of a characteristic energy and then measuring the flux of electrons leaving the surface. The energy spectrum for the ejected electrons is a combination of a number of factors, particularly resonance structures that derive from the electronic states of the material being analyzed.

In particular, the presence of certain peaks at certain binding energies identifies the presence of specific elements in the composition being tested. The amplitude of those peaks is in turn directly related to the amount of the element present in the tested area of the sample.

FIG. 4 accordingly illustrates that palladium is a major component of the composition, along with a much smaller amount of iron.

The magnetic characteristics were collected using a vibrating sample magnetometer (vsm) at room temperature.

Example 2

The composition produced in Example 1 was used as a catalyst in a microwave-assisted Heck reaction coupling using the following illustrated reaction scheme.

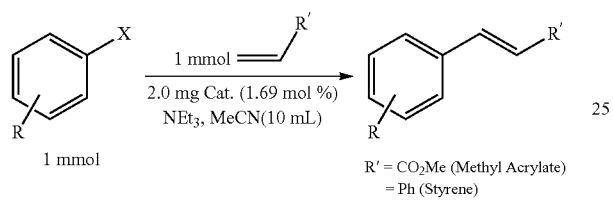

R' = CO₂Me (Methyl Acrylate)
  = Ph (Styrene)

Using the composition of Example 1 as the catalyst and applying microwave radiation using the previously-described CEM DISCOVER® instrument produced the following results for the indicated structures. The microwave power was adjusted to reach and maintain the indicated temperatures.

| —R | —X | Olefin | Temp (C.) | Time (min) | Run 1 | Run 2 | Run 3 | Isolated |
|---|---|---|---|---|---|---|---|---|
| p-MeO | I | MA | 140 | 30 | 100 | 100 | 100 | 96 |
| p-MeO | I | Styrene | 140 | 90 | 94 | 97 | 95 | 87 |
| p-C(O)Me | I | MA | 140 | 15 | 100 | 100 | 100 | 92 |
| m-CO2Me | I | MA | 140 | 15 | 100 | 100 | 100 | 99 |
| m-CO2Me | I | Styrene | 140 | 30 | 100 | 100 | 100 | 97 |

In related experiments to date, where the aromatic compound included bromine as the halogen, the conversion rate was low; i.e. between about 10 and 20%, and it appears that an entirely different reaction may be taking place. Where the halogen was chlorine, no reaction appeared to take place.

Example 3

The composition produced according to Example 1 was similarly used to catalyze the hydrogenation of the following five compounds. In each case, the hydrogenation was carried out under microwave irradiation in an ethyl acetate solvent (10 mL) using 2.0 mg of the palladium-iron oxide catalyst (with the exception of compound E in which 4.0 mg were used) representing approximately 1.3 mole percent and carried out at 80° C. As in the previous example, the microwave power was adjusted to reach and maintain the indicated temperature.

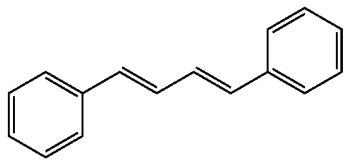
A

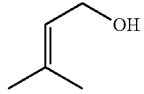
B

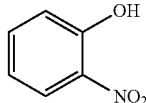
C

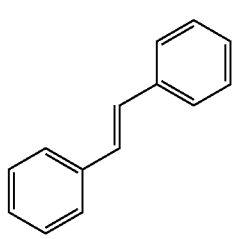
D

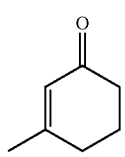
E

| Compound | Time (min) | Pressure (Psi H₂) | Run 1 | Run 2 | Run 3 | Isolated |
|---|---|---|---|---|---|---|
| A | 10 | 50 | 100 | 100 | 100 | 98 |
| B | 90 | 100 | 75 | 75 | 76 | n/a |
| C | 25 | 50 | 100 | 100 | 100 | 89 |
| D | 60 | 100 | 100 | 100 | 100 | 100 |
| E | 120 | 100 | 100 | 94 | 87 | 96 |
| Cholesterol | 120 | 100 | 0 | | | |

Example 4

Turnover

Figure 7:
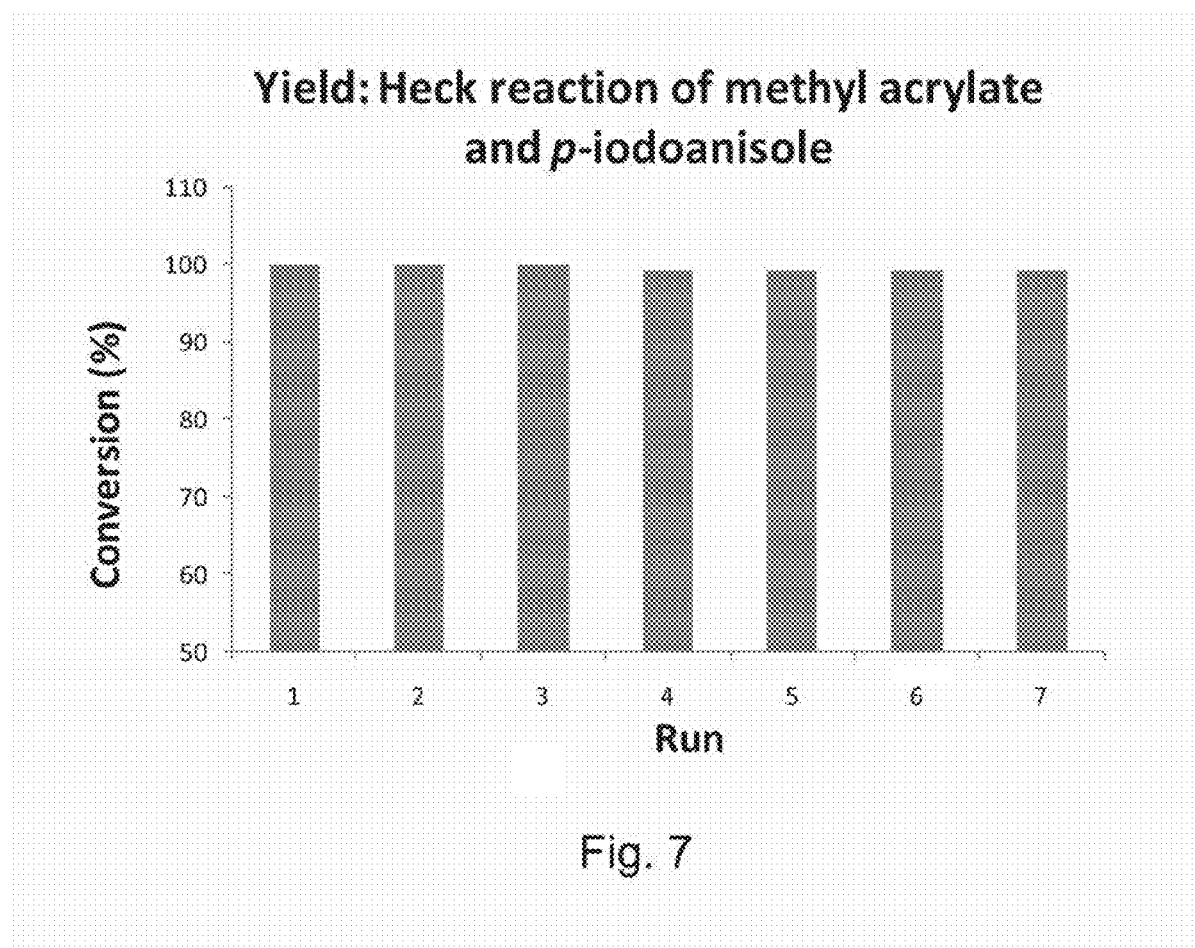
FIG. 7 is a plot of conversion percentage versus number of runs using the catalyst according to the present invention.

FIG. 7 is a plot of reaction conversion plotted against repeated runs to illustrate the favorable turnover characteristics of the invention. In a manner consistent with Example 2, methyl acrylate and p-iodoanisole were coupled in a Heck-type reaction using the catalyst of the present invention.

After each run, a magnet was placed at the bottom of the 35 mL vial to hold the stir bar (and catalyst that had become magnetically attached to the stir bar) down while the solution was decanted. A new solution of starting material was added, and the reaction repeated. This was done a total of 7 times using the same catalyst sample; i.e., without using a new batch of catalyst. The initial amount of catalyst was 1.69 mol %. At the end, 7 mmol of starting material was converted to product. This represents a turnover number of 7/0.0169; i.e., 414. Thus, even after 7 runs, the catalyst retained excellent activity.

Example 5

Microwave Versus Conventional Preparation

The Heck reaction of Example 4 was repeated using 7 mg (5.14 mmol) of the catalyst composition of the invention as prepared using microwave synthesis (in the same manner as Example 2) and as prepared using conventional heating. The results were as follows:

| Catalyst Preparation Method | Time | Yield | Pd Leached (ug) | Weight % Lost |
|---|---|---|---|---|
| Microwave | 30 | >99 | 72 ppm (36.25) | 0.54 |
| Conventional | 30 | >99 | 172 ppm (86.75 | 1.29 |

Example 6

Comparison of Pd—$Fe_2O_3$ Catalyst with Pd/C Catalyst

Two experiments were carried out in which para-iodoanisole and methyl acrylate were combined in a Heck reaction. In the first, the Pd—$Fe_2O_3$ catalyst of the present invention was used (7 mg; 5.14 mmol) and in the second a more conventional palladium on carbon catalyst was used (in a 10% by weight amount). In both cases, the reactions were carried out under microwave irradiation (CEM DISCOVER® instrument; power adjusted based on temperature) at a maximum temperature of 140° C. for 30 minutes in the presence of the respective catalyst and solvents.

The results are set forth in the following table:

| Catalyst | Amount (mg; mmole Pd) | Pd in crude (ppm; ug) | Conversion (%) |
|---|---|---|---|
| Pd—Fe2O3 | 7; 0.0514 | 72; 36.25 | >99 |
| Pd/C | 54; 0.0514 | 300; 150 | 70 |

Example 7

Open Vessel Heck Reaction

Four experiments were carried out combining methyl-3-iodobenzoate with styrene in a Heck coupling. In each case, 2.0 millimoles of each compound were used as starting material. In a first group of two experiments, 10 mg (4 mole percent) of the catalyst according to the present invention was used. In one of these, the reaction was carried out in an oil bath and in the other the reaction was carried out using microwave irradiation (CEM DISCOVER® instrument; 300 watts of constant power; 2.45 GHz). Using the oil bath, the conversion was 28% and using the microwaves the conversion was 59%.

In a second group of two experiments, the same reactions were carried out under the same conditions, but using 30 mg of the catalyst (12 mole percent). After seven hours the conversion rate in the oil bath was 63% and the conversion rate using microwave irradiation (in the same manner) was 89%. This demonstrated both the value of the catalyst and the advantage and selectivity of microwave heating. Although the inventors do not wish to be found by any particular theory, it appears that the microwaves may selectively heat the catalyst in a manner that enhances the overall reaction rate.

In summary, the composition of the present invention, and the associated methods of synthesis and use, provide a greener catalyst synthesis route; provide efficient catalytic activity; provide for quick and easy catalyst separation using magnetic techniques based upon the magnetic properties of the composition; and demonstrate the ease of use and reuse that together indicate substantial potential for scale up reactions.

In the drawings and specification there have been set forth exemplary embodiments of the invention, and although specific terms have been employed, they are used in a generic and descriptive sense only and not for purposes of limitation, the scope of the invention being defined in the claims.

The invention claimed is:

1. A composition comprising:
    particles of an intermetallic magnetic compound of iron oxide and palladium
    having a nanometer particle size; and
    wherein at least about 70% by weight of the palladium present in the particles is present on the surface of the nanometer size particles.

2. A composition according to claim 1 wherein the iron oxide is predominantly $Fe_2O_3$.

3. A composition according to claim 1 having a formula palladium x (iron oxide) 1-x where x is at least 0.7.

4. A composition according to claim 3 where x is at least about 0.9.

5. A composition according to claim 1 wherein at least about 90% by weight of the palladium present in the particles is present on the surface of the nanometer size particles.

6. A composition according to claim 1 wherein the particle size is below 50 nm.

7. A composition according to claim 1 wherein the particle size is below 20 nm.

8. A composition according to claim 1 wherein the particle size is between about 5 and 10 nm.

9. A composition according to claim 1 wherein:
    the iron oxide is predominantly $Fe_2O_3$;
    the composition has a mole fraction of palladium of at least 0.70;
    and
    the particle size is below 20 nm.

10. A composition comprising:
    particles of an intermetallic magnetic compound of iron oxide and palladium;
    wherein the iron oxide is predominantly $Fe_2O_3$;
    the mole fraction of palladium in said compound is at least about 0.70;
    at least about 70% by weight of the palladium present in the particles is present on the surface of the nanometer size particles; and
    the particle size is below 20 nanometers.

11. A composition according to claim 10 comprising:
    a mole fraction of palladium of at least about 0.90;
    at least about 90% by weight of the palladium present in the particles is present on the surface of the nanometer size particles; and
    the particle size is between about 5 and 10 nanometers.

* * * * *